US00PP08200P

United States Patent [19]

Moore

[11] Patent Number: Plant 8,200

[45] Date of Patent: Apr. 13, 1993

[54] MINIATURE ROSE PLANT NAMED 'MORYOU'

[75] Inventor: Ralph S. Moore, Visalia, Calif.

[73] Assignee: Sequoia Nursery, Visalia, Calif.

[21] Appl. No.: 799,968

[22] Filed: Nov. 29, 1991

[51] Int. Cl.[5] ..... A01H 5/00

[52] U.S. Cl. ..... Plt./10

[58] Field of Search ..... Plt./7.1, 9, 10

*Primary Examiner*—Howard J. Locker

[57] ABSTRACT

This invention relates to a new and distinct variety of miniature rose plant primarily identified by its deep pink to medium red buds and flowers and hybrid tea form.

1 Drawing Sheet

The present invention relates to a new and distinct variety of hardy, dwarf, bush type rose plant of the miniature class; the variety being primarily characterized—as to novelty—by the deep pink to red buds and flowers which generally are of exhibition (Hybrid Tea) form.

The variety is further characterized by:

An abundance of bloom, with flowers often borne singly and also several to the stem in loose clusters.

Little or no fragrance.

A plant which is vigorous, of rounded, upright shape with medium size, semi-glossy to matte foliage with pointed leaflets; the buds and flowers being similar in form and size to Sheri Anne (Miniature—U.S. Plant Pat. No. 3,826).

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between Orangeade (Floribunda—not patented) as the seed parent and Rainbow's End (miniature—U.S. Plant Pat. No. 5,482) as the pollen parent.

Subsequent to origination of the variety I successfully asexually reproduced it at the same nursery, located as aforesaid, by budding as well as by cuttings; the reproductions having run true in all respects.

The color photograph illustrates the variety, including the foliage, buds and flowers.

Referring now specifically to the new and distinct variety of minature rose plant, the following is a detailed description thereof in outline; all major color plate identifications being by reference to the British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature.

*Variety identification.*—Moryou. (Commercial synonym: Just For You).

Flowers borne: Singly and several together (3 to 5) on slender wirey stems.

Quality of bloom: Abundant both outside and in greenhouse.

Bud:

*Sepals.*—Permanent; spear shaped; recurved.

*Peduncle.*—Medium to long; slender but sturdy; erect; medium to light green, sometimes tinted bronze (outdoors); with no prickles and numerous very short hairs.

*Before calyx breaks.*—Size — small. Form long; pointed with several foliaceous apendages on surface of bud; with foliaceous parts extending beyond the tip of the bud equal to one-half or less of its length. Color — medium green, occasionally tinted with bronze (outdoors).

*As calyx breaks.*—Color — red. Opening: opens well in all weather.

Bloom:

*Size when fully open.*—Small, averaging about 40 mm to 45 mm ($1\frac{3}{4}''$).

*Petalage.*—Double — averaging about 20–25 petals, arranged regularly plus several small petaloids. Form — high centered with petals rolled loosely outward and downward. Open flowers may show stamens.

Petals: Fairly thick; velvety on inside and satiny on outside surface.

*Shape.*—Outside petals, broad lanceolate with small acute tip; intermediate — broad lanceolate with rounded tip; inside — lanceolate with rounded or very short acute tip.

*Color.*—Newly opened flower from a plant grown in plastic greenhouse (September 1991), Visalia, Calif. Outside petal: Outside surface — near Rose Red 724/3 with a slight blueish cast (or undertone) and often with very fine blackish veining, becoming yellowish near base. Inside surface — near Rose Red 724 (with slight orangish undertone and often with very fine blackish veining) becoming whiteish to yellow at base. Intermediate petal: Outside surface similar to outside petal. Inside surface similar to outside petal. Inner petal: Outside surface — same as intermediate petal; inside surface — same as intermediate petal. General color effect; buds and newly opened flowers — deep pink to medium red with lighter reverse. Note: Color can vary slightly, depending upon weather, time of year, light intensity, etc. Three days open — color — similar to newly opened flowers, but lighter color. Behavior — opens well in all weather. Spent petals drop off. Flower longevity (September 1991) — plant in pot 6–8 days or longer.

Cut flowers at living room temperature 4–5 days or longer.

Reproductive organs:

*Stamens.*—Arranged regularly about pistils.

*Filaments.*—Varying length, medium long, yellow.

*Anthers.*—Well formed; yellow.

*Pollen.*—Some.

*Pistils.*—Average number.

*Styles.*—Varying length — medium long; reddish; bunched.

*Ovaries.*—All enclosed in calyx.

*Hips.*—None.

*Seed.*—None.

Foliage:

*Leaves.*—Compound of five (sometimes three or seven) leaflets; medium size; leathery; semi-glossy to matte.

*Leaflets.*—Shape: broad, nearly oval; apex acute; base rounded; well serrated. Color: medium green; new growth — normal (medium)green (sometimes tinted reddish). Rachis: medium strength; upper side may have few or no tiny prickles and several short hairs; grooved; underside may have few or no thorns and few or no tiny prickles or hairs. Stipules: short length; medium width; short to medium length narrow points which turn out usually at more than 45 degrees.

Growth:

*Habit.*—Dwarf; bushy; upright; much branched.

*Growth.*—Free; vigorous; internodes short.

*Canes.*—Medium; slender; sturdy.

*Main stems.*—Color: medium green.

*Thorns.*—few, medium to long, usually straight. Prickles — none. Hairs — none.

*Branches.*—Color: medium green. Thorns: few; slender; medium to long — straight. Prickles: none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, substantially as illustrated and described, characterized by buds and flowers of exhibition form, essentially deep pink to red in color, with reverse of petals being a slightly lighter shade of red, and further characterized by the plant being of compact well rounded shape, vigorous, with the main stems and shoots being usually sparsley thorny, said plant being easy to propagate from cuttings or by budding, with an abundance of medium to small semi-glossy to matte foliage and an abundance of flowers borne singly or several to the stem in loose clusters.

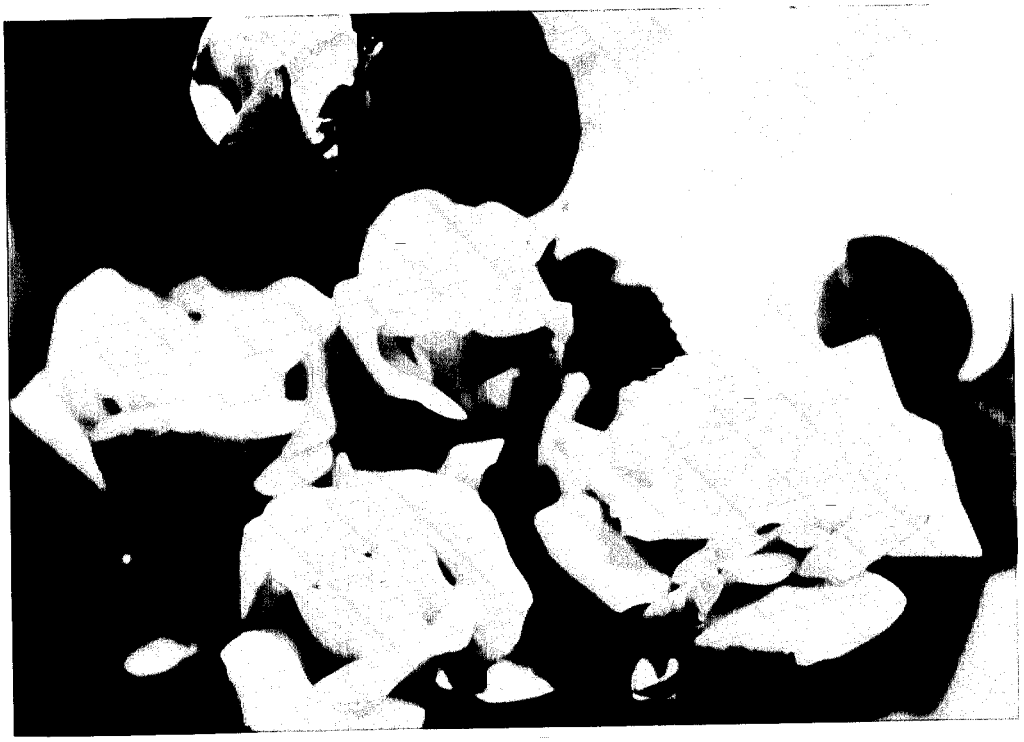

* * * * *